US011713475B2

(12) United States Patent
Jennewein et al.

(10) Patent No.: US 11,713,475 B2
(45) Date of Patent: Aug. 1, 2023

(54) FERMENTATIVE PRODUCTION OF OLIGOSACCHARIDES BY TOTAL FERMENTATION UTILIZING A MIXED FEEDSTOCK

(71) Applicant: Chr. Hansen HMO GmbH, Rheinbreitbach (DE)

(72) Inventors: Stefan Jennewein, Bad Honnef (DE); Dirk Wartenberg, Gau-Algesheim (DE); Katja Parschat, Bonn (DE)

(73) Assignee: Chr. Hansen HMO GmbH, Rheinbreitbach (DE)

( * ) Notice: Subject to any disclaimer, the term of this patent is extended or adjusted under 35 U.S.C. 154(b) by 0 days.

(21) Appl. No.: 17/273,447

(22) PCT Filed: Sep. 2, 2019

(86) PCT No.: PCT/EP2019/073363
§ 371 (c)(1),
(2) Date: Mar. 4, 2021

(87) PCT Pub. No.: WO2020/048927
PCT Pub. Date: Mar. 12, 2020

(65) Prior Publication Data
US 2021/0317493 A1 Oct. 14, 2021

(30) Foreign Application Priority Data
Sep. 6, 2018 (EP) ..................................... 18192898

(51) Int. Cl.
| | |
|---|---|
| *C12N 9/90* | (2006.01) |
| *C12P 19/12* | (2006.01) |
| *C12N 1/20* | (2006.01) |
| *C12N 9/10* | (2006.01) |
| *C12N 9/12* | (2006.01) |
| *C12N 9/16* | (2006.01) |
| *C12P 19/04* | (2006.01) |
| *C12P 19/18* | (2006.01) |

(52) U.S. Cl.
CPC ............... *C12P 19/12* (2013.01); *C12N 1/20* (2013.01); *C12N 9/1051* (2013.01); *C12N 9/1205* (2013.01); *C12N 9/16* (2013.01); *C12N 9/90* (2013.01); *C12P 19/04* (2013.01); *C12P 19/18* (2013.01); *C12N 2500/34* (2013.01); *C12Y 204/01038* (2013.01); *C12Y 207/01004* (2013.01); *C12Y 207/01011* (2013.01); *C12Y 207/01056* (2013.01); *C12Y 207/07009* (2013.01); *C12Y 301/03011* (2013.01); *C12Y 501/03002* (2013.01); *C12Y 504/02002* (2013.01)

(58) Field of Classification Search
CPC ........................................................ C12N 9/90
See application file for complete search history.

(56) References Cited

U.S. PATENT DOCUMENTS

| | | |
|---|---|---|
| 7,521,212 B1 | 4/2009 | Samain |
| 2011/0207187 A1 | 8/2011 | Tokuda et al. |
| 2014/0349348 A1* | 11/2014 | Beauprez ................ C12P 19/04 435/100 |
| 2021/0317493 A1* | 10/2021 | Jennewein ............... C12N 9/90 |

FOREIGN PATENT DOCUMENTS

| | | |
|---|---|---|
| RU | 2016121174 C2 | 10/2020 |
| WO | 2006034225 A2 | 3/2006 |
| WO | 2015066551 A2 | 5/2015 |
| WO | 2015150328 A1 | 10/2015 |

OTHER PUBLICATIONS

Bidossi et al., "Afunctional genomics approach to establish teh complement of carbohydrate transpoerters in *Strerptococcus pneumoniae*", PLoS ONE 7(3): e33320 (2012) (Year: 2012).*
Gen Bank Accession No. AAA27691.1, published Apr. 26, 1993 (Year: 1993).*
Gen Bank Accession No. ANK03259.1, published Jun. 15, 2016 (Year: 2016).*
Gen Bank Accession No. AUY31240.1, published Mar. 2, 2018 (Year: 2018).*
R. E. Huber, et al., "Efflux of beta-galactosidase products from *Escherichia coli*," Journal of Bacteriology, (1980), vol. 141, No. 2:528-533.
Mara Grube et al., "Hydrogen-producing *Escherichia coli* strains overexpressing lactose permease FT-IR analysis of the lactose-induced stress," Biotechnology and Applied Biochemistry, (2014), vol. 61, No. 2, 111-117.
International Search Report for Application No. PCT/EP2019/073363 dated Nov. 13, 2019.
Albermann et al., "Synthesis of the milk oligosacaride 2'-fucosyl-lactose using recombinant bacterial enzymes" Carbohydrate Rese (2001) vol. 334, No. 2: 97-103.
Bäcklund, "Impact of glucose uptake rate on recombinant protein production in *Escherichia coli*," Thesis, Royal Institute of Technology, 2011, 77 pages.
Crigler et al., "Glucose can be transported and utilized in *Escherichia coli* by an altered or overproduced N-acetylglucosamine phosphotransferase system (PTS)," Microbiology, 2018, 164:163-172.
Curtis et al., "Phosphorylation of D-glucose in *Escherichia coli* mutants defective in glucosephsophotransferase, mannosephosphatetransferase and glucokinase," J Bacteriology, 1975, 122(3):1189-1199.

(Continued)

*Primary Examiner* — Tekchand Saidha
(74) *Attorney, Agent, or Firm* — McNeill Baur PLLC

(57) ABSTRACT

Disclosed are genetically engineered microbial cells for the production of oligosaccharides comprising a galactose-β1, 4-glucose moiety at their reducing end, wherein said microbial cells are able to produce said oligosaccharides in the absence of exogenously added lactose, and a method of producing said oligosaccharides using said microbial cells.

19 Claims, 4 Drawing Sheets

(56) References Cited

OTHER PUBLICATIONS

Fordjour et al., "Metabolic engineering of *Escherichia coli* BL21 (DE3) for de novo production of l-DOPA from d-glucose,," Microb Cell Fact, 2019, 118:74, 10 pages.

* cited by examiner

FERMENTATIVE PRODUCTION OF OLIGOSACCHARIDES BY TOTAL FERMENTATION UTILIZING A MIXED FEEDSTOCK

CROSS-REFERENCE TO RELATED APPLICATIONS

This application is the National Stage entry of International Application No. PCT/EP2019/073363, filed 2 Sep. 2019, which claims priority to European Patent Application No. 18192898.7, filed 6 Sep. 2018.

BACKGROUND

Field

The present invention relates to bacterial host cells being capable to produce lactose or an oligosaccharide of interest which comprises a galactose-β1,4-glucose moiety at its reducing end, as well as to a method of producing lactose or an oligosaccharide of interest which comprises a terminal galactose-β1,4-glucose moiety.

Description of Related Art

Human milk comprises a complex mixture of carbohydrates, fats, proteins, vitamins, minerals and trace elements. The most predominant fraction of human milk consists of carbohydrates. The fraction of carbohydrates within human milk can be further divided into (i) lactose and (ii) oligosaccharides (human milk oligosaccharides, HMOs). Whereas lactose (galactose-β1,4-glucose) is used as an energy source, the oligosaccharides are not metabolized by the infant. The fraction of oligosaccharides accounts for up to ⅒ of the total carbohydrate fraction and consists of probably more than 150 different oligosaccharides. The occurrence and concentration of these complex oligosaccharides are specific to humans and thus cannot be found in large quantities in the milk of other mammals including dairy farm animals.

The most prominent human milk oligosaccharides are 2'-fucosyllactose and 3'-fucosyllactose which together can contribute up to ⅓ of the total HMO fraction. Further prominent HMOs present in human milk are lacto-N-tetraose, lacto-N-neotetraose and the lacto-N-fucopentaose I. Besides these neutral oligosaccharides, also acidic HMOs can be found in human milk such as 3'-sialyllactose, 6'-sialyllactose and 3-fucosyl-3'-sialyllactose, sialyl-lacto-N-tetraose, disialyl-lacto-N-tetraose. Notably, the vast majority of HMOs comprise a galactose-β1,4-glucose moiety at their reducing end. The structures of the HMOs are closely related to epitopes of epithelial cell surface glycoconjugates, the Lewis histoblood group antigens such as Lewis x (LeX). The structural similarity of HMOs to epithelial epitopes accounts for the HMOs protective properties against bacterial pathogens.

The presence of oligosaccharides in human milk is known for a long time and the physiological functions of these oligosaccharides were subject to medical research for many decades. For some of the more abundant human milk oligosaccharides, specific functions have already been identified.

Besides the local effects in the intestinal tract as mentioned herein before, HMOs have also been shown to elicit systemic effects in infants by entering their systemic circulation. Also, the impact of HMOs on protein-carbohydrate interactions, e.g. selectin-leukocyte binding, can modulate immune responses and reduce inflammatory responses. In addition, it becomes more and more recognized that HMOs represent a key substrate for the development of infants' microbiomes.

Due to the well-studied beneficial properties of prebiotic oligosaccharides, in particular of HMOs, but their limited availability from natural sources, an efficient commercial, i.e. large-scale, production of HMOs is highly desirable.

Attempting for large scale production of individual human milk oligosaccharides, chemical routes to some of these oligosaccharides were developed. However, such methods involve the use of several noxious chemicals, which impose the risk to contaminate the final product. At least large-scale quantities as well as qualities sufficient for food applications cannot be provided until today through chemical synthesis.

To bypass the drawbacks associated with the chemical synthesis of human milk oligosaccharides, several enzymatic methods and fermentative approaches for their production were developed. Fermentative production processes have been developed for several HMOs such as 2'-fucosyllactose, 3-fucosyllactose, lacto-N-tetraose, lacto-N-neotetraose, 3'-sialyllactose and 6'-sialyllactose. These production processes typically use genetically engineered bacterial strains such as recombinant *Escherichia coli*.

Today, all fermentative production processes as well as biocatalytic reactions to produce HMOs are based exclusively on exogenously added lactose as the starting substrate. One or more monosaccharides are added to lactose in the processes (U.S. Pat. No. 7,521,212 B1; Albermann et al., (2001) *Carbohydr. Res.* 334(2) p 97-103). The addition of monosaccharides to lactose can either be catalyzed by glycosyltransferases or by glycosidases using suitable activated monosaccharide substrates. In addition, additional monosaccharides can be added to lactose by transglucosidase reactions.

In particular the fermentative production of HMOs proved to be efficient, because the nucleotide activated monosaccharides that are required but difficult to synthesize are provided by the metabolism of the microbial cells that are employed. However, the use of whole cells for the synthesis of HMOs also bears—in comparison to the biocatalytic approach—several major disadvantages, which relate to transport processes across the cell membrane, to metabolic side reactions and to the necessity that the oligosaccharides being synthesized by the microbial cells have to be purified from a complex mixture containing, inter alia, various polyols (e.g. carbohydrates), nucleic acids, polypeptides, inorganic material, etc.

A technical problem related to the use of lactose in fermentative processes that needs to be overcome, in particular when the oligosaccharide to be produced shall be used in human consumption, is the rearrangement of lactose (beta-D-galacto-pyranosyl-(1→4)-D-glucose) into lactulose (beta-D-galactopyranosyl-(1→4)-D-fructofuranose) upon thermal treatment of lactose. This rearrangement can occur extensively by heat sterilization of lactose, leading to the rearrangement of several percent of the lactose to be present in the fermentation medium or the lactose fermentation feed to lactulose. However, lactulose is a non-digestible sugar for humans and is widely used as laxative in the treatment of chronic constipation.

The conversion of lactose to lactulose not only leads to the generation of undesired lactulose, but also provides an undesired substrate for glycosylation reactions in the microbial cells. Thereby, more complex oligosaccharides (e.g.

2'-fucosyl-lactulose) are generated as by-products. Thus, the generation of lactulose from lactose is leading to the contamination of the desired product with closely related oligosaccharides, which are difficult or even impossible to separate from the desired product.

Furthermore, lactose can be converted to allolactose (beta-D-galactopyranosyl-(1→6)-D-glucopyranose), another unwanted contaminant (Huber et al., "Efflux of beta-galactosidase products from *Escherichia coli*" (1980) J. Bacteriol. 141, 528-533), if supplied to a beta-galactosidase positive *E. coli* strain.

Moreover, the addition of lactose may cause a well-documented effect known as "lactose induced cell killing". This effect is most likely caused by the excessive uptake of lactose by the microbial cell and the associated collapse of the proton gradient across the bacterial membrane. In particular the overexpression of the lactose permease gene (e.g. lacY of *E. coli*) in combination with the exposure of the recombinant microbial cell to excess lactose can cause a considerable growth delay of the recombinant strain and an increased synthesis of cellular polysaccharides (Grube et al., "Hydrogen-producing *Escherichia coli* strains overexpressing lactose permease: FT-IR analysis of the lactose-induced stress" (2013) Biotechnol. Appl. Biochem. 5, 31).

Furthermore, any commercially available lactose today is derived from whey, a waste product of the dairy industry. Whey is produced in enormous quantities in cheese and casein manufacturing. Thus, being derived from the dairy industry there are still concerns related to a potential contamination of lactose with prion proteins which are the causative agent of bovine spongiform encephalopathy (BSE), also widely known as mad cow disease. BSE is a fatal neurodegenerative disease in cattle, causing spongy degeneration of the brain and spinal cord. BSE can be trans-mitted to humans and is there known as variant of Creutzfeldt-Jakob disease.

Above all, lactose is still one of the most expensive components of the fermentation medium and its substitution by glucose, glycerol, sucrose etc. would lead to a more cost-efficient production of HMOs.

To overcome aforementioned drawbacks, improved means and methods for the production of HMOs were developed. For example, WO 2015/150328 A1 discloses bacterial host cells being capable to produce oligosaccharides comprising a terminal galactose-(1→4)-glucose disaccharide, wherein said bacterial host cell expresses at least one recombinant nucleic acid sequence encoding for a β-1,4-galactosyltransferase which is able to galactosylate a free glucose monosaccharide to intracellularly generate lactose, and which contains and expresses at least one recombinant nucleic acid sequence encoding a fucosyltransferase, a sialyltransferase, a glucosamyltransferase or a galactosyltransferase. Said bacterial host cell is capable of generating the oligosaccharide without exogenous addition of lactose such that the bacterial host cell can be cultivated in a culture medium without exogenous addition of lactose to produce said oligosaccharide. More specifically, WO 2015/150328 A1 discloses a genetically engineered *E. coli* strain for the production of 2'-fucosyllactose which utilizes sucrose or a combination of glucose and sucrose as carbon source. For utilization of sucrose, said *E. coli* strain was genetically engineered to expresses the four genes of the csc-gene cluster of *E. coli* W, i.e. the genes encoding the sucrose permease (cscB), the fructokinase (cscK), the sucrose hydrolase (cscA), and a transcriptional repressor (cscR).

However, producing 2'-FL by said genetically engineered *E. coli* strain using sucrose as sole carbon and energy source has its drawbacks in that it is also difficult to heat sterilize sucrose without a considerable degree of hydrolyzation and formation of unwanted side products. As an alternative sterile filtration of sucrose solution can be employed, but the sterile filtration bears a high risk of foreign growth contamination of the fermentation in particular in industrial-scale fermentation.

In addition, cultivating a microbial cell for the production of an HMO in the presence of sucrose as carbon source, wherein said microbial cell has been genetically engineered to possess a split metabolism such that the monomers constituting sucrose are used in distinct metabolic pathways, leads to undesired growth characteristics of the bacterial cell culture, presumably due to the stoichiometry of monomers generated from intracellular sucrose hydrolyzation which does not match the quantitative needs of the different monomers in the distinct pathways.

To overcome aforementioned drawbacks, a genetically engineered microbial cell is provided which is capable of producing an oligosaccharide of interest comprising a galactose-β1,4-glucose moiety at its reducing end when cultivated on a mixed monosaccharide feedstock as main carbon and energy source but in the absence of exogenously added lactose.

SUMMARY

In a first aspect, provided is a genetically engineered microbial cell for the production of lactose or an oligosaccharide of interest comprising a galactose-β1,4-glucose moiety at its reducing end, wherein said microbial cell is capable of producing said lactose de novo or said oligosaccharide of interest when cultivated in the absence of exogenously added lactose.

In a second aspect, provided is the use of the genetically engineered microbial host cell for the production of lactose or an oligosaccharide of interest comprising a galactose-β1, 4-glucose moiety at its reducing end.

In a third aspect, provided is a method for the production of lactose or an oligosaccharide of interest comprising a galactose-β1,4-glucose moiety at its reducing end by cultivating the genetically engineered microbial cell in the presence of a mixed feedstock containing glucose, and recovering the oligosaccharide of interest.

DETAILED DESCRIPTION

Figure 1:
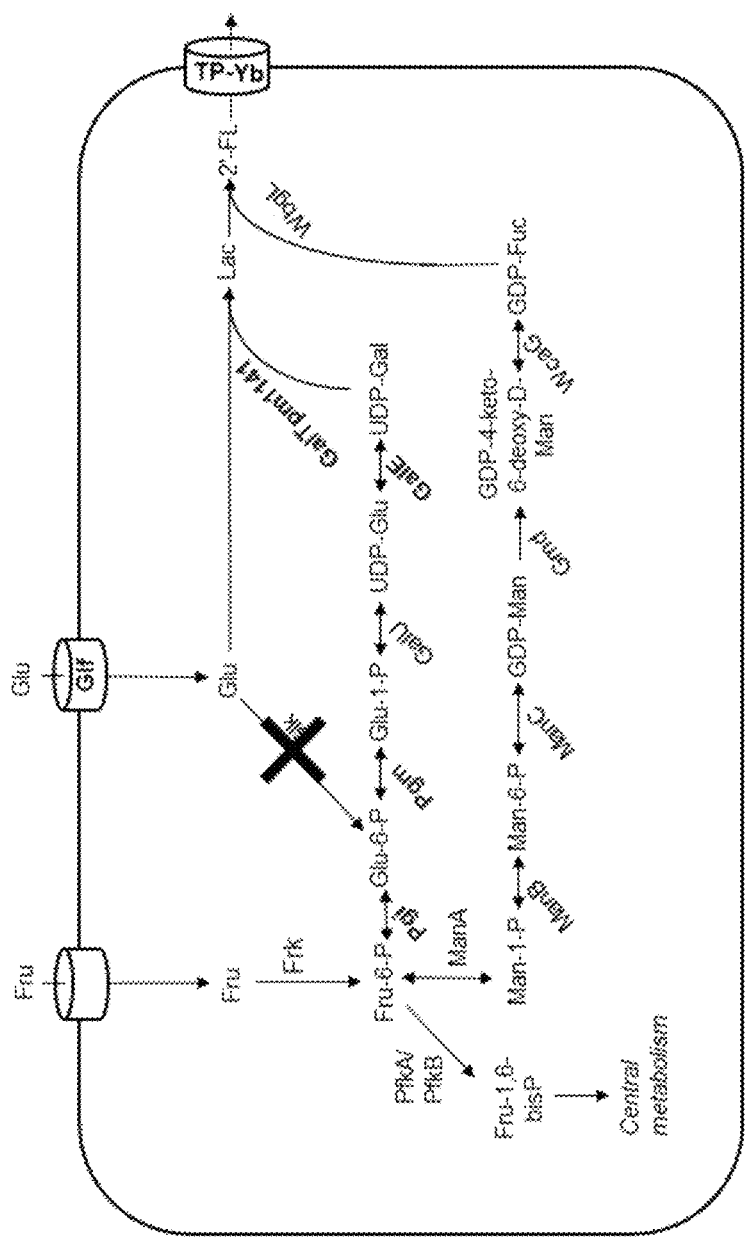
FIG. 1 shows a schematic drawing of an exemplary embodiment of a genetically engineered microbial cell according to the invention for the production of 2'-fucosyl-lactose.

According to the first aspect, provided is a genetically engineered microbial cell for the production of lactose or an oligosaccharide of interest comprising a galactose-β1,4-glucose moiety at its reducing end, wherein said microbial cell possesses at least one glucose transporter for translocating glucose from the culture medium into the cytoplasm of the microbial cell, a UDP-galactose biosynthesis pathway for intracellular biosynthesis of UDP-galactose, and at least one galactosyltransferase that is able to galactosylate free intracellular glucose to intracellularly produce lactose.

The genetically engineered microbial cell is able to produce lactose. In certain embodiments, the microbial cell can utilize the lactose being produced by itself for the production of an oligosaccharide of interest which bears a galactose-β1,4-glucose moiety at its reducing end. For the production of said oligosaccharide of interest, it is not necessary to provide an exogenous supply of lactose to the microbial cell.

The genetically engineered microbial cell possesses at least one glucose transporter for translocating glucose from the culture medium said microbial cell is cultivated in into the cytoplasm of the microbial cell such that free glucose becomes available for intracellular biosynthesis of lactose.

Typically, the genetically engineered microbial cell comprises at least one functional gene encoding said glucose transporter which is able to translocate glucose (Glu) from the culture medium into the cell's cytoplasm.

The term "functional gene" as used herein, refers to a nucleic acid molecule comprising a nucleotide sequence which encodes a protein or polypeptide, and which also contains regulatory sequences operably linked to said protein-coding nucleotide sequence such that the nucleotide sequence which encodes the protein or polypeptide can be expressed in/by the microbial cell bearing said functional gene. Thus, when cultivated at conditions that are permissive for the expression of the functional gene, said functional gene is expressed, and the microbial cell expressing said functional gene typically comprises the protein or polypeptide that is encoded by the protein coding region of the functional gene. As used herein, the terms "nucleic acid" and "polynucleotide" refer to a deoxyribonucleotide or ribonucleotide polymer in either single- or double-stranded form, and unless otherwise limited, encompasses known analogues of natural nucleotides that hybridize to nucleic acids in a manner similar to naturally occurring nucleotides. Unless otherwise indicated, a particular nucleic acid sequence includes the complementary sequence thereof.

The term "operably linked" as used herein, shall mean a functional linkage between a nucleic acid expression control sequence (such as a promoter, signal sequence, or array of transcription factor binding sites) and a second nucleic acid sequence, wherein the expression control sequence affects transcription and/or translation of the nucleic acid corresponding to the second sequence. Accordingly, the term "Promoter" designates DNA sequences which usually "precede" a gene in a DNA polymer and provide a site for initiation of the transcription into mRNA. "Regulator" DNA sequences, also usually "upstream" of (i.e., preceding) a gene in a given DNA polymer, bind proteins that determine the frequency (or rate) of transcriptional initiation. Collectively referred to as "promoter/regulator" or "control" DNA sequence, these sequences which precede a selected gene (or series of genes) in a functional DNA polymer cooperate to determine whether the transcription (and eventual expression) of a gene will occur. DNA sequences which "follow" a gene in a DNA polymer and provide a signal for termination of the transcription into mRNA are referred to as transcription "terminator" sequences.

The term "recombinant", as used herein with reference to a bacterial host cell indicates that the bacterial cell replicates a heterologous nucleic acid, or expresses a peptide or protein encoded by a heterologous nucleic acid (i.e., a sequence "foreign to said cell"). Recombinant cells can contain genes that are not found within the native (non-recombinant) form of the cell. Recombinant cells can also contain genes found in the native form of the cell wherein the genes are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, and related techniques. Accordingly, a "recombinant polypeptide" is one which has been produced by a recombinant cell. A "heterologous sequence" or a "heterologous nucleic acid", as used herein, is one that originates from a source foreign to the particular host cell (e.g. from a different species), or, if from the same source, is modified from its original form. Thus, a heterologous nucleic acid operably linked to a promoter is from a source different from that from which the promoter was derived, or, if from the same source, is modified from its original form. The heterologous sequence may be stably introduced, e.g. by transfection, transformation, conjugation or transduction, into the genome of the host microorganism cell, wherein techniques may be applied which will depend on the host cell the sequence is to be introduced. Various techniques are known to a person skilled in the art and are, e.g., disclosed in Sambrook et al., Molecular Cloning: A Laboratory Manual, 2nd Ed., Cold Spring Harbor Laboratory Press, Cold Spring Harbor, N.Y. (1989).

Accordingly, a "genetically engineered microbial cell" is understood as a bacterial cell which has been transformed or transfected, or is capable of transformation or transfection by an exogenous polynucleotide sequence.

Thus, the nucleic acid sequences as used in the present invention, may, e.g., be comprised in a vector which is to be stably transformed/transfected or otherwise introduced into host microorganism cells.

A great variety of expression systems can be used to produce the polypeptides of the invention. Such vectors include, among others, chromosomal, episomal and virus-derived vectors, e.g., vectors derived from bacterial plasmids, from bacteriophage, from transposons, from yeast episomes, from insertion elements, from yeast chromosomal elements, from viruses, and vectors derived from combinations thereof, such as those derived from plasmid and bacteriophage genetic elements, such as cosmids and phagemids. The expression system constructs may contain control regions that regulate as well as engender expression. Generally, any system or vector suitable to maintain, propagate or express polynucleotides and to synthesize a polypeptide in a host may be used for expression in this regard. The appropriate DNA sequence may be inserted into the expression system by any of a variety of well-known and routine techniques, such as, for example, those set forth in Sambrook et al., supra.

The art is rich in patent and literature publications relating to "recombinant DNA" methodologies for the isolation, synthesis, purification and amplification of genetic materials for use in the transformation of selected host organisms. Thus, it is common knowledge to transform host organisms with "hybrid" viral or circular plasmid DNA which includes selected exogenous (i.e. foreign or "heterologous") DNA sequences. The procedures known in the art first involve generation of a transformation vector by enzymatically cleaving circular viral or plasmid DNA to form linear DNA strands. Selected foreign DNA strands usually including sequences coding for desired protein product are prepared in linear form through use of the same/similar enzymes. The linear viral or plasmid DNA is incubated with the foreign DNA in the presence of ligating enzymes capable of effecting a restoration process and "hybrid" vectors are formed which include the selected exogenous DNA segment "spliced" into the viral or circular DNA plasmid.

The term "nucleotide sequence encoding . . . " generally refers to any polyribonucleotide or polydeoxyribonucleotide, which may be unmodified RNA or DNA or modified RNA or DNA, and generally represents the portion of a gene which encodes a certain polypeptide or protein. The term includes, without limitation, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded regions, or a mixture of single- and double-stranded regions. The term also encompasses polynucleotides that include a single continuous region or discontinuous regions encoding the polypeptide (for example, interrupted by integrated phage or an insertion sequence or editing) together with additional regions that also may contain coding and/or non-coding sequences.

In an embodiment, a suitable glucose transporter is a glucose facilitated diffusion protein. A suitable glucose facilitated fusion protein is encoded by the glf gene of *Zymomonas mobilis* subsp. *mobilis* (strain ATCC 31821/ZM4/CP4).

In an additional and/or alternative embodiment, another suitable glucose transporter is a glucose translocation permease. A suitable glucose translocation permease is encoded by the *E. coli* K-12 galP gene. The glucose translocation permease is also known as galactose-proton symporter or galactose premease, but also imports glucose across the cell membrane.

Thus, in an additional and/or alternative embodiment, the genetically engineered microbial cell comprises and expresses at least one gene comprising the protein coding region of the glf gene of *Zymomonas mobilis* subsp. *mobilis* (strain ATCC 31821/ZM4/CP4), the *E. coli* K-12 galP gene or functional variants thereof.

The term "variant(s)" as used herein, refers to a polynucleotide or polypeptide that differs from a reference polynucleotide or polypeptide respectively, but retains the essential (enzymatic) properties of the reference polynucleotide or polypeptide. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques, by direct synthesis, and by other recombinant methods known to the persons skilled in the art.

Within the scope of the present invention, also nucleic acid/polynucleotide and polypeptide polymorphic variants, alleles, mutants, and interspecies homologs are comprised by those terms, that have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of at least about 25, 50, 100, 200, 500, 1000, or more amino acids, to a polypeptide encoded by a wildtype protein.

Accordingly, a "functional variant" of any of the genes/proteins disclosed therein, is meant to designate sequence variants of the genes/proteins still retaining the same or somewhat lesser activity of the gene or protein the respective fragment is derived from.

The genetically engineered microbial cell possesses an UDP-galactose biosynthesis pathway for intracellular formation of GDP-galactose (GDP-Gal), because an efficient supply of UDP-galactose is needed for intracellular biosynthesis of lactose.

In an additional and/or alternative embodiment, UDP-galactose can be obtained from the microbial cells' own metabolism, i.e. the activity of a phosphoglucomutase, an UTP-glucose-1-phosphate-uridyltransferase and an UDP-glucose-4-epimerase.

The intracellular supply of GDP-galactose can be improved by genetic modifications such as an expression or overexpression of one or more of the genes encoding polypeptides exhibiting phosphoglucomutase activity, UDP-glucose-1-phosphate-uridyltransferase activity and UDP-glucose-4-epimerase activity, respectively.

The term "overexpression" or "overexpressed" as used herein refers to a level of enzyme or polypeptide expression that is greater than what is measured in a wildtype cell of the same species as the host cell that has not been genetically altered.

Phosphoglucomutase is an enzyme that facilitates interconversion of glucose-1-phosphate to glucose-6-phosphate in that it on an α-D-glucose monomer from the 1' to the 6' position or the 6' to the 1' position. An exemplary gene encoding a suitable phosphoglucomutase is the *E. coli* K-12 pgm gene (GenBank: U08369.1). Thus, in an additional and/or alternative embodiment, the genetically engineered microbial cell comprises and expresses/overexpresses a gene encoding a phosphoglucomutase, the gene preferably comprising the protein coding region of the *E. coli* pgm gene or a variant thereof.

UTP-glucose-1-phosphate-uridyltransferase such as GalU or a functional variant thereof catalyzes the conversion of α-D-glucose-1-phosphate to UDP-glucose utilizing UTP. An exemplary gene encoding a suitable UTP-glucose-1-phosphate-uridyltransferase is the *E. coli* K-12 galU gene (GenBank: M98830.1). Thus, in an additional and/or alternative embodiment, the genertically engineered microbial cell comprises and expresses/overexpresses a gene encoding a UTP-glucose-1-phosphate-uridyltransferase, the gene preferably comprising the protein coding region of the *E. coli* galU gene or a variant thereof.

UDP-glucose-4-epimerase such as GalE or a functional variant thereof catalyzes the epimerization of UDP-glucose to UDP-galactose. An exemplary gene encoding a UDP-glucose-4-epimerase is the *E. coli* K-12 galE gene. Thus, in an additional and/or alternative embodiment, the genertically engineered microbial cell comprises and expresses/overexpresses a gene encoding an UDP-glucose-4-epimerase, the gene preferably comprising the protein coding region of the *E. coli* galE gene or a variant thereof.

In an additional and/or alternative embodiment, the UDP-galactose biosynthesis pathway additionally comprises the enzymatic activity of a glucose-6-phosphate isomerase which converts fructose-6-phosphate to glucose-6-phosphate and vice versa. An exemplary gene encoding a glucose-6-phosphate isomerase is the *E. coli* K-12 pgi gene. Thus, in an additional and/or alternative embodiment, the genertically engineered microbial cell comprises and expresses/overexpresses a gene encoding a glucose-6-phosphate isomerase, the gene preferably comprising the protein coding region of the *E. coli* pgi gene or a variant thereof.

Alternatively, UDP-galactose can be obtained by feeding galactose to the microbial cells via the culture medium. The galactose is taken up by the cell and phosphorylated to galactose-1-phosphate which is then converted to UDP-galactose. Genes encoding the enzymes possessing the required enzymatic activities are known in the literature (Groissoird et al., "Characterization, Expression, and Mutation of the *Lactococcus lactis* galPMKTE Genes, Involved in Galactose Utilization via the Leloir Pathway (2003) *J. Bacteriol.* 185(3) 870-878).

The genetically engineered microbial cell comprises a β-1,4-galactosyltransferase that is able to galactosylate free glucose monosaccharide. In an additional and/or alternative embodiment, a suitable β-1,4-galactosyltransferase is derived from *Neisseria menningitidis*, from *Aggregatibacter aphrophilus* of from *Pasteurella multocida*, preferably a β-1,4-galactosyltransferase encoded by the *Neisseria menningitidis* IgtB gene, by the lex-1 gene of *Aggregatibacter aphrophilus* or by the β-1,4-galactosyltransferase gene galTpm1141 from *Pasteurella multocida* (GenBank: AEC04686). Thus, in an additional and/or alternative embodiment, the genertically engineered microbial cell comprises and expresses/overexpresses a gene encoding a β-1,4-galactosyltransferase, the gene preferably comprising the protein coding region of the *Neisseria menningitidis* IgtB gene, the *Aggregatibacter aphrophilus* lex-1 gene, the *Pasteurella multocida* galTpm1141 gene or a variant thereof.

The β-1,4-galactosyltransferase uses UDP-galactose as substrate for the transfer of the galactose moiety to the free glucose monosaccharide thereby synthesizing a galactose-β1,4-glucose disaccharide, i.e. lactose.

In an additional and/or alternative embodiment, the genetically engineered microbial cell comprises at least one additional glycosyltransferase, i. e. in addition to said β-1, 4-galactosyltransferase.

Generally, and throughout the present disclosure, the term "glycosyltransferase activity" or "glycosyltransferase" designates and encompasses enzymes that are responsible for the biosynthesis of disaccharides, oligosaccharides and polysaccharides, and they catalyze the transfer of monosaccharide moieties from an activated nucleotide monosaccharide/sugar (the "glycosyl donor") to a glycosyl acceptor molecule.

In a preferred embodiment, the at least one additional glycosyltransferase is a fucosyltransferase, a sialyltransferase, a glucosaminyltransferase or a galactosyltransferase, more preferably, the at least one additional glycosyltransferase is selected from at least one of the following: alpha-1,2-fucosyltransferase, alpha-1,3-fucosyltransferase, beta-1,3-N-acetylglucosamyltransferase, beta-1,3-galactosyltransferase, alpha-2,3-sialyltransferase, alpha-2,6-sialyltansferase, beta-1,4-galactosyltransferase or beta-1,6-galactosyltransferase.

The enzymatic activity of the at least one additional glycosyltransferase allows production of oligosaccharides of interest which comprise a galactose-β-1,4-glucose moiety at their reducing end by using lactose as an acceptor for the activity of the additional glycosyltransferase. Table 1 identifies the most abundant HMOs which may be produced by the microbial cells and methods disclosed herein as oligosaccharide of interest.

TABLE 1

List of oligosaccharides of interest that can be produced by using a genetically modified microbial cell and/or a method as described herein.

| Name | Abbrev. | structure |
|---|---|---|
| 2'-Fucosyllactose | 2'-FL | Fuc(α1-2)Gal(β1-4)Glu |
| 3-Fucosyllactose | 3-FL | Gal(β1-4)Glu<br>        \|<br>Fuc(α1-3) |
| 2',3-Difucosyllactose | DF-L | Fuc(α1-2)Gal(β1-4)Glu<br>                   \|<br>                Fuc(α1-3) |
| Lacto-N-triose II | LNT II | GlcNAc(β1-3)Gal(β1-4)Glu |
| Lacto-N-tetraose | LNT | Gal(β1-3)GlcNAc(β1-3)Gal(β1-4)Glu |
| Lacto-N-neotetraose | LNnT | Gal(β1-4)GlcNAc(β1-3)Gal(β1-4)Glu |
| Lacto-N-fucopentaose I | LNFP I | Fuc(αβ1-2)Gal(β1-3)GlcNAc(β1-3)Gal(β1-4)Glu |
| Lacto-N-neofucopentaose I | LNnFP I | Fuc(α1-2)Gal(β1-4)GlcNAc(β1-3)Gal(β1-4)Glu |
| Lacto-N-fucopentaose II | LNFP II | Gal(β1-3)GlcNAc(β1-3)Gal(β1-4)Glu<br>               \|<br>        Fuc(α1-4) |
| Lacto-N-fucopentaose III | LNFP III | Gal(β1-4)GlcNAc(β1-3)Gal(β1-4)Glu<br>               \|<br>       Fuc(α1-3) |

TABLE 1-continued

List of oligosaccharides of interest that can be produced by using a genetically modified microbial cell and/or a method as described herein.

| Name | Abbrev. | structure |
|---|---|---|
| Lacto-N-fucopentaose V | LNFP V | Gal(β1-3)GlcNAc(β1-3)Gal(β1-4)Glu<br>\|<br>Fuc(α1-3) |
| Lacto-N-neofucopentaose V | LNnFP V | Gal(β1-4)GlcNAc(β1-3)Gal(β1-4)Glu<br>\|<br>Fuc(α1-3) |
| Lacto-N-difucohexaose I | LNDH I | Gal(β1-3)GlcNAc(β1-3)Gal(β1-4)Glu<br>\|  \|<br>Fuc(α1-2) Fuc(α1-4) |
| Lacto-N-difucohexaose II | LND | Gal(β1-3)GlcNAc(β1-3)Gal(β1-4)Glu<br>\|             \|<br>Fuc(α1-4)        Fuc(α1-3) |
| 6'-Galactosyllactose | 6'-GL | Gal(β1-6)Gal(β1-4)Glu |
| 3'-Galactosyllactose | 3'-GL | Gal(β1-3)Gal(β1-4)Glu |
| Lacto-N-hexaose | LNH | Gal(β1-4)GlcNAc(β1-6)Gal(β1-4)Glu<br>\|<br>Gal(β1-3)GlcNAc(β1-3) |
| Lacto-N-neohexaose | LNnH | Gal(β1-4)GlcNAc(β1-6)Gal(β1-4)Glu<br>\|<br>Gal(β1-4)GlcNAc(β1-3) |
| para-Lacto-N-hexaose | paraLNT | Gal(β1-3)GlcNAc(β1-3)Gal(β1-4)GlcNAc(β1-3)Gal(β1-4)Glu |
| para-Lacto-N-neohexaose | paraLNnH | Gal(β1-4)GlcNAc(β1-3)Gal(β1-4)GlcNAc(β1-3)Gal(β1-4)Glu |
| Difucosyl-lacto-N-neohexaose | DF-LNnH | Fuc(α1-3)<br>\|<br>Gal(β1-4)GlcNAc(β1-6)Gal(β1-4)Glu<br>\|<br>Gal(β1-4)GlcNAc(β1-3)<br>\|<br>Fuc(α1-3) |
| 3'-Sialyllactose | 3'-SL | Neu5Ac(α2-3)Gal(β1-4)Glu |
| 6'-Sialyllactose | 6'-SL | Neu5Ac(α2-6)Gal(β1-4)Glu |
| Lacto-N-sialylpentaose a | LST-a | Neu5Ac(α2-3)Gal(β1-3)GlcNAc(β1-3)Gal(β1-4)Glu |
| Lacto-N-sialylpentaose b | LST-b | Gal(β1-3)GlcNAc(β1-3)Gal(β1-4)Glu<br>\|<br>Neu5Ac(α2-6) |
| Lacto-N-sialylpentaose c | LST-c | Neu5Ac(α2-6)Gal(β1-4)GlcNAc(β1-3)Gal(β1-4)Glu |
| Fucosyl-lacto-N-sialylpentaose a | F-LST-a | Neu5Ac(α2-3)Gal(β1-3)GlcNAc(β1-3)Gal(β1-4)Glu<br>\|<br>Fuc(α1-4) |
| Fucosyl-lacto-N-sialylpentaose b | F-LST-b | Fuc(α1-2)Gal(β1-3)GlcNAc(β1-3)Gal(β1-4)Glu<br>\|<br>Neu5Ac(α2-6) |
| Fucosyl-lacto-N-sialylpentaose c | F-LST-c | Neu5Ac(α2-3)Gal(β1-3)GlcNAc(β1-3)Gal(β1-4)Glu<br>\|<br>Fuc(α1-3) |
| Disialyl-lacto-N-tetraose | DS-LNT | Neu5Ac(α2-3)Gal(β1-4)GlcNAc(β1-3)Gal(β1-4)Glu<br>\|<br>Neu5Ac(α2-6) |

TABLE 1-continued

List of oligosaccharides of interest that can be produced by using a
genetically modified microbial cell and/or a method as described herein.

| Name | Abbrev. | structure |
|---|---|---|
| Disialyl-lacto-N-fucopentaose | DS-LNFP V | Neu5Ac(α2-3)Gal(β1-4)GlcNAc(β1-3)Gal(β1-4)Glu<br>        |                                        |<br>Neu5Ac(α2-6)            Fuc(α1-3) |
| 3-Fucosyl-3'-sialyllactose | 3F-3'-SL | Neu5Ac(α2-3)Gal(β1-4)Glu<br>                     |<br>               Fuc(α1-3) |
| 3-Fucosyl-6'-sialyllactose | 3F-6'-SL | Neu5Ac(α2-6)Gal(β1-4)Glu<br>                     |<br>               Fuc(α1-3) |
| Lacto-N-neodifucohexaose I | LNnDFH I | Gal(β1-4)GalNAc(β1-3)Gal(β1-4)Glu<br>       |                              |<br>Fuc(α1-3)         Fuc(α1-3) |

In an additional and/or alternative embodiment, the microbial cell comprises a glucose-translocating phosphotransferase system (PtsG). The glucose-translocating phosphotransferase system catalyzes the phosphorylation of incoming glucose concomitantly with its translocation across the cell membrane.

The general mechanism of the Pts system is the following: a phosphoryl group from phosphoenolpyruvate (PEP) is transferred via a signal transduction pathway, to enzyme I (EI) which in turn transfers it to a phosphoryl carrier, the histidine protein (HPr). Phospho-HPr then transfers the phosphoryl group to a sugar-specific permease, a membrane-bound complex known as enzyme 2 (EII), which transports the sugar to the cell. EII consists of at least three structurally distinct domains IIA, IIB and IIC. These can either be fused together in a single polypeptide chain or exist as two or three interactive chains, formerly called enzymes II (EII) and III (EIII).

The first domain (IIA or EIIA) carries the first permease-specific phosphorylation site, a histidine which is phosphorylated by phospho-HPr. The second domain (IIB or EIIB) is phosphorylated by phospho-IIA on a cysteinyl or histidyl residue, depending on the sugar transported. Finally, the phosphoryl group is transferred from the IIB domain to the sugar substrate concomitantly with the sugar uptake processed by the IIC domain. This third domain (IIC or EIIC) forms the translocation channel and the specific substrate-binding site.

Thus, the PtsG system acquires exogenous glucose and provides glucose-6-phosphate in the microbial cell. Glucose-6-phosphate can either be utilized in the UDP-galactose biosynthesis pathway and/or converted to fructose-6-phosphate which in turn may be used for generating energy-rich triphosphates in the central metabolism and/or, for example, in the biosynthesis of nucleotide activated saccharides such as GDP-fucose.

In an additional and/or alternative embodiment, the glucokinase gene(s) of the microbial cell have been deleted or functionally inactivated such that the microbial cell does not possess any polypeptide having glucokinase activity. Glucokinase (Glk)b phosphorylates free glucose at its carbon atom 6 to generate glucose-6-phosphate. In the absence of glucokinase activity, free glucose that is translocated into the microbial cell's cytoplasm becomes available as substrate for the β1,4-galactosyltransferase to produce lactose, whereas the glucose-6-phosphate obtained from PtsG activity may be utilized for UDP-galactose formation or other metabolic pathways.

In an additional and/or alternative embodiment, the genetically engineered microbial cell comprises a fructose transporter for translocating fructose (Fru) from the culture medium into the microbial cell's cytoplasm. A suitable fructose transporter for uptake of free fructose is an isoform (PtsG-F) as described by Kornberg et al. PNAS 97: 1808-1812 (2000)).

The internalized fructose may then be phosphorylated by a fructokinase (FrK) to provide fructose-6-phosphate (Fru-6-P). Fructose-6-phosphate may be utilized in the UDP-galactose biosynthesis pathway and/or in other metabolic pathways such as generating energy-rich triphosphates in the central metabolism and/or, for example, in the biosynthesis of nucleotide activated saccharides such as GDP-fucose.

In an additional and/or alternative embodiment, the genetically engineered microbial cell comprises polypeptides exhibiting fructokinase-6 activity and polypeptides exhibiting 6-phosphofructokinase-1 activity (FruK or phosphofructokinase) to provide a metabolic pathway from internalized fructose via fructose-6-phosphate to fructose-1.6-bisphosphate.

In an additional and/or alternative embodiment, the genetically engineered microbial cell comprises a fructose-translocating phosphotransferase system (PtsF). The fructose-translocating phosphotransferase system catalyzes the phosphorylation of incoming fructose concomitantly with its translocation across the cell membrane.

Thus, the PtsF system acquires exogenous fructose and provides fructose-1-phosphate in the microbial cell. The PtsF system comprises a membrane-spanning protein FruA, a 1-phosphofructose kinase (FruK) and a diphosphoryl transfer protein FruB. Fructose is translocated by means of FruA and FruB to provide fructose-1-phosphate in the cytoplasm. Fructose-1-phosphate can be further phosphorylated by a phosphofructokinase (FruK) to yield fructose-1,6-bisphosphate which in turn may be used by the microbial cell for generating energy-rich triphosphates in the central metabolism.

Another suitable PtsF System comprises LevD, LevE, LevF and LevG. LevD is the fructose-specific phosphotransferase enzyme IIA component. LevE is the fructose-specific phosphotransferase enzyme IIB component. LevF is the fructose permease IIC component, LevG is the fructose permease IID component. Corresponding genes levD, levE, levF and levG are—for example known form *Bacillus subtilis* (strain 168). Said PtsF system provides fructose-1-phosphate in the cell.

In an additional and/or alternative embodiment, the genetically engineered microbial cell comprises at least one 1-phosphofructokinase (FruK).

In an additional and/or alternative embodiment, the genetically engineered microbial cell comprises a fructose-1,6-bisphosphatase (GlpX). Said fructose-1,6-bisphosphatase dephosphorylates fructose-1,6-bisphosphate to provide fructose-6-phosphate. The fructose-6-phosphate may be used by the microbial cell in the GDP-galactose biosynthesis pathway or in another metabolic pathway for example, in the biosynthesis of nucleotide activated saccharides such as GDP-fucose.

Preferably, the microbial cell also comprises a deletion or functional inactivation of its phosphofructokinase gene(s). Deletion or functional inactivation of the phosphofructokinase gene(s) leads to a microbial cell that lacks phosphofructokinase activity such that the conversion of Fru-6-P to Fru-1,6-bisP is prevented. In *E. coli*, two isoforms of phosphofructokinase are present, designated PfkA and PfkB. The corresponding genes are pfkA and pfkB.

In an additional and/or alternative embodiment, the genetically engineered microbial cell possesses a GDP-L-fucose biosynthesis pathway. In an additional and/or alternative embodiment, the GPD-fucose biosynthesis pathway comprises a mannose-6-phosphate isomerase (ManA), a phosphomannomutase (ManB), a mannose-1-phosphate-guanylyltransferase (ManC), a GDP-mannose-4,6-dehydratase (Gmd), a GDP-L-fucose synthase (WcaG). Preferably, the microbial cell possessing a GDP-L-fucose biosynthesis pathway also possesses a fucosyltransferase.

In an additional and/or alternative embodiment, the microbial cell comprises an exporter protein or a permease exporting the oligosaccharide of interest from the cell, preferably a sugar efflux transporter.

In an additional and/or alternative embodiment, the genetically engineered microbial cell comprises a deletion of functional inactivation of its glucose-6-phosphate isomerase gene such that the microbial cell lacks glucose-6-phosphate isomerase activity. Glucose-6-phosphate isomerase, in *E. coli* designated Pgi, converts glucose-6-phosphate to fructose-6-phosphate. By deleting the glucose-6-phosphate gene(s) or by inactivating their expression, any glucose-6-phosphate present in the cytoplasm of the microbial cell can be directed towards lactose production.

In an additional and/or alternative embodiment, the microbial cell is a bacterial cell selected from the group consisting of bacteria of the genera *Escherichia, Lactobacillus, Corynebacterium, Bacillus, Streptococcus, Enterococcus, Lactococcus* and *Clostidium*, preferably a bacterial cell that is selected from the group of bacterial species consisting of *Escherichia coli, Corynebacterium glutamicum, Clotridium cellulolyticum, Clostridium ljungdahlii, Clostridium autoethanogenum, Clostridium acetobutylicum, Bacillus subtilis, Bacillus megaterium, Lactobacillus casei, Lactobacillus acidophilus, Lactobacillus helveticus, Lactobacillus delbrueckii,* and *Lactococcus lactis*. In another embodiment, the microbial cell is an *Escherichia coli*. A person skilled in the art will be aware of further bacterial strains when reading the present disclosure.

According to the second aspect, provided is the use of a genetically engineered microbial cell as described herein for the production of lactose or an oligosaccharide of which comprises a galactose-β1,4-glucose moiety at its reducing end. In an additional and/or alternative embodiment, the genetically engineered microbial cell is used in a method for the production of lactose or an oligosaccharide of which comprises a galactose-β1,4-glucose moiety at its reducing end, wherein the microbial cell is cultivated in the presence of a mixed feedstock comprising glucose and at least one additional carbon source. Said additional carbon source may be selected from the group consisting of fructose, galactose, mannose, xylose, rhamnose, glycerol, succinate, pyruvate and malate. Preferably, the mixed feedstock is a mixture of glucose and fructose, more preferably an equimolar mixture of glucose and fructose, most preferably comprising or consisting of hydrolyzed sucrose.

According to the third aspect, provided is a method for the production of lactose or an oligosaccharide of interest which comprises a galactose-β1,4-glucose moiety at its reducing end, the method comprising the steps of:
a) providing a genetically engineered microbial cell as described herein;
b) cultivating the microbial cell in a culture medium and under conditions that are permissive for the production of said lactose or oligosaccharide of interest, wherein the culture medium contains a mixture of glucose and at least one additional compound selected from the group consisting of fructose, galactose, mannose, xylose, rhamnose, glycerol, succinate, pyruvate and malate as main carbon source; and
c) recovering the lactose or oligosaccharide of interest from the culture medium and/or the microbial cell.

In an additional and/or alternative embodiment, the oligosaccharide of interest is a human milk oligosaccharide selected from the group consisting of 2'-fucosyllactose, 3-fucosyllactose, 2',3-difucosyllactose, 3'-sialyllactose, 6'-sialyllactose, 3-fucosyl-3'-sialyllactose, lacto-N-tetraose, lacto-N-neotetraose, lacto-N-fucopentaose I, lacto-N-fucopentaose II, lacto-N-fucopentaose III, lacto-N-fucopentaose V, lacto-N-difucosylhexose I, lacto-N-difucosylhexaose II, lacto-N-sialylpentaose LSTa, LSTb, LSTc.

Preferably, the mixture of glucose and at least one additional monosaccharide is a mixed feedstock of glucose and fructose, preferably obtained by hydrolyzation of sucrose.

In an additional and/or alternative embodiment, the microbial cell is cultivated without exogenous supply of lactose, in particular when cultivated for the production of the oligosaccharide of interest.

The present invention will be described with respect to particular embodiments and with reference to drawings, but the invention is not limited thereto but only by the claims. Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

Furthermore, some of the embodiments are described herein as a method or combination of elements of a method that can be implemented by a processor of a computer system or by other means of carrying out the function. Thus, a processor with the necessary instructions for carrying out such a method or element of a method forms a means for carrying out the method or element of a method.

Furthermore, an element described herein of an apparatus embodiment is an example of a means for carrying out the function performed by the element for the purpose of carrying out the invention.

In the description and drawings provided herein, numerous specific details are set forth. However, it is understood that embodiments of the invention may be practiced without these specific details. In other instances, well-known methods, structures and techniques have not been shown in detail in order not to obscure an understanding of this description.

The invention will now be described by a detailed description of several embodiments of the invention. It is clear that other embodiments of the invention can be configured according to the knowledge of persons skilled in the art without departing from the true spirit or technical teaching of the invention, the invention being limited only by the terms of the appended claims.

In an embodiment, an $E.\ coli$ strain possessing the genotype lacY$^-$, lacZ$^-$, fuclK$^-$, wcaJ$^-$ is metabolically engineered to efficiently produce 2'-fucosyllactose by means of total fermentation using a mixed-monosaccharide feedstock (e.g. hydrolyzed sucrose) as main carbon- and energy source. Therefore, the expression of the glucokinase gene gik and/or the glucose dehydrogenase gene gcd and/or the glucose PTS permease gene ptsG is decreased and/or abolished. In addition, a glucose permease gene is expressed or overexpressed in said $E.\ coli$ strain.

Furthermore, at least one of the $E.\ coli$ genes manA, manC, manB, gmd, wcaG, pgm, galU and galE as well as the expression of a heterologous β-1,4-galactosyltransferase, capable to transfer galactose from UDP-galactose on glucose, thus generating lactose, and a α-1,2-fucosyltransferase, capable to transfer fucose from GDP-fucose to lactose, thus generating 2'-fucosyllactose, are expressed/overexpressed.

In a preferred embodiment, this production strain is further engineered by decreasing and/or diminishing the expression of the phosphofructokinase genes pfkA and/or pfkB and/or the glucose-6-phosphate dehydrogenase gene zwf and/or the glucose-6-phosphate isomerase gene pgi. This further genetic modification allows cultivation of the thus engineered production strain on a mixed-monosaccharide feedstock (e.g. hydrolyzed sucrose) as main carbon- and energy source, while preventing to hamper the strain's metabolism but increasing precursor supply (glucose and fructose-6-phosphate and glucose-6-phosphate) for 2'-fucosyllactose production by total fermentation.

Referring to FIG. 1, a exemplary microbial cell of the invention is schematically shown. Said microbial cell is capable of producing 2'-FL when cultivated on a mixed feedstock consisting of glucose (Glu) and fructose (Fru), but which mixed feedstock does not contain lactose (Lac). The microbial cell expresses polynucleotides encoding a glucose transporter (Glf) and a fructose transporter for import of glucose and fructose into the cell respectively. As expression of the glucosekinase Glk has been abolished by deletion or functional inactivation of the g/k gene(s), any glucose that is imported by the cell becomes available as substrate for the β1,4-galactosyltransferase GalTpm1141 by the UDP-galactose biosynthesis pathway to intracellularly generate lactose (Lac).

Imported fructose is phosphorylated by the cell's fructose-6 kinase to generate a intracellular Fru-6-P pool. A portion of the Fru-6-P pool is used in the "UDP-Gal biosynthesis pathway" to intracellularly synthesize UDP-Gal which serves as Gal donor for the GalTpm1141 galactosyltransferase to generate Lac. Another portion of the fru-6-P pool is used in the "GDP-L-Fuc biosynthesis pathway" for GDP-L-fucose production. Said GDP-L-fucose serves as fucose donor for the 2'-fucosyltransferase WbgL. Yet a third portion of the intracellular Fru-6-P pool is used for energy and biomass production in that its fru-6-P is converted to Fru-1,6-bisP by the cells phosphofructokinases PfkA and/or PfkB.

Figure 2:
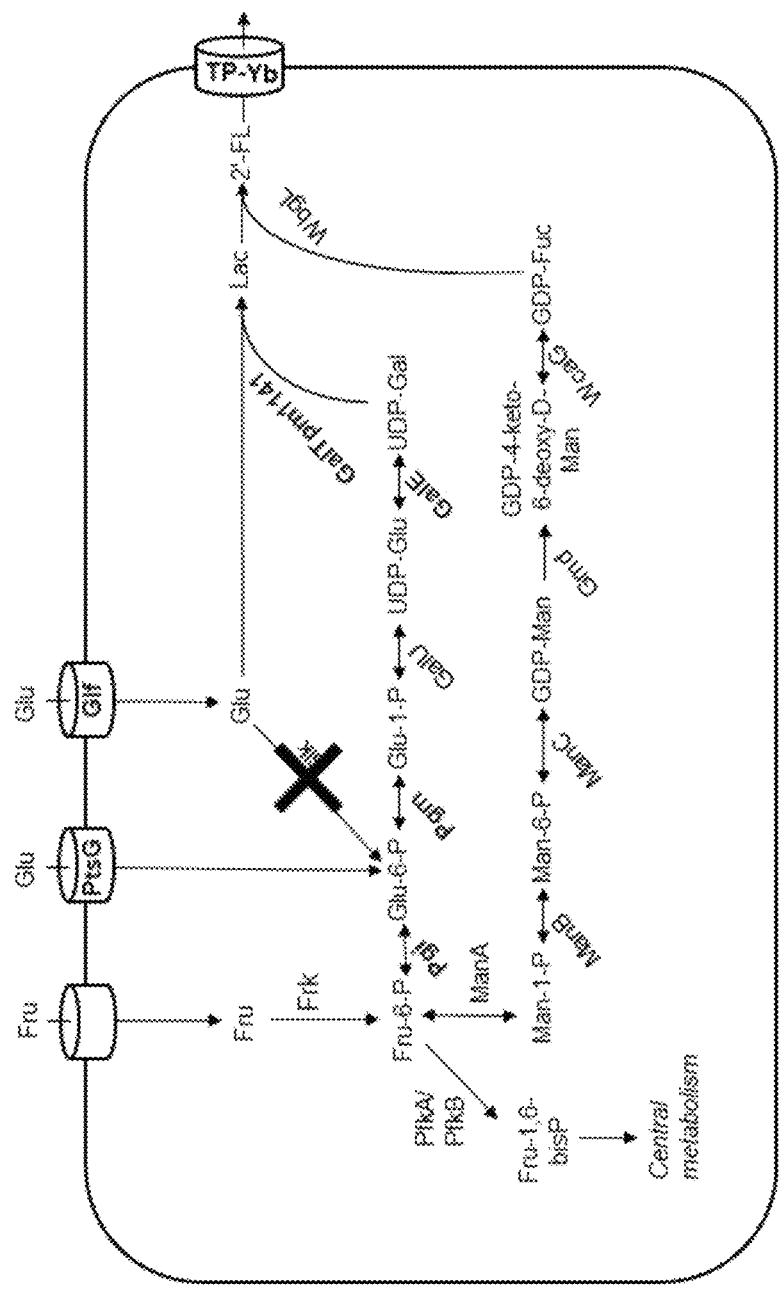
FIG. 2 shows a schematic drawing of another exemplary embodiment of a genetically engineered microbial cell according to the invention for the production of 2'-fucosyl-lactose.

FIG. 2 displays schematically another a exemplary microbial cell of the invention being capable of producing 2'-FL when cultivated on a mixed feedstock consisting of glucose (Glu) and fructose (Fru), but which mixed feedstock does not contain lactose (Lac). In addition to the exemplary microbial cell shown in FIG. 1, the microbial cell further comprises a glucose-specific Pts System (PtsG). Said PtsG system imports and phosphorylates Glu to provide Glu-6-P in the cell's cytosol. Said Glu-6-P may be utilized by the microbial cell for generating UDP-Gal or Fru-6-P. In a variant of the microbial cell (not shown), the cell's pgi gene(s) encoding a glucose-6-phosphate isomerase (Pgi) is deleted. Along with the deletion of the glk gene, the microbial has been genetically engineered such that free glucose monomer as acquired by Glf becomes available as substrate to the β1,4-galactosyltransferase, whereas any Glu-6-P acquired by means of PtsG becomes available for UDP-Gal biosynthesis.

Figure 3:
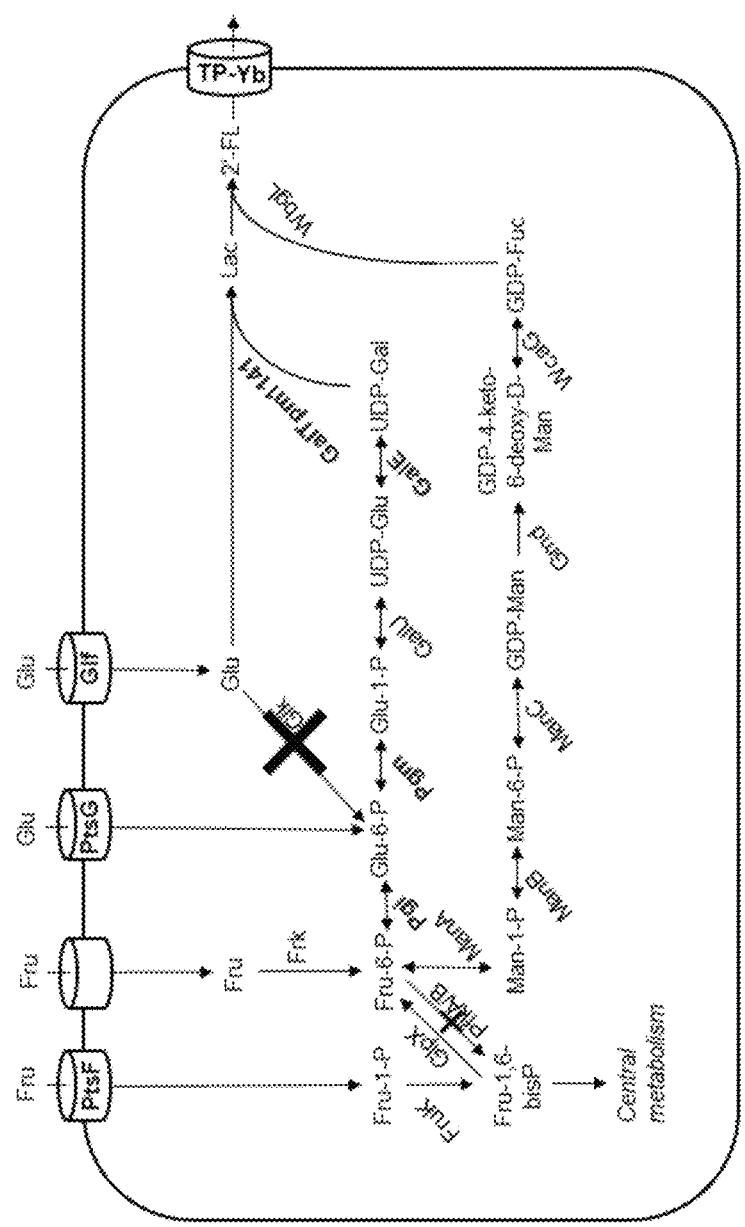
FIG. 3 shows a schematic drawing of a further exemplary embodiment of a genetically engineered microbial cell according to the invention for the production of 2'-fucosyl-lactose.
Figure 4:
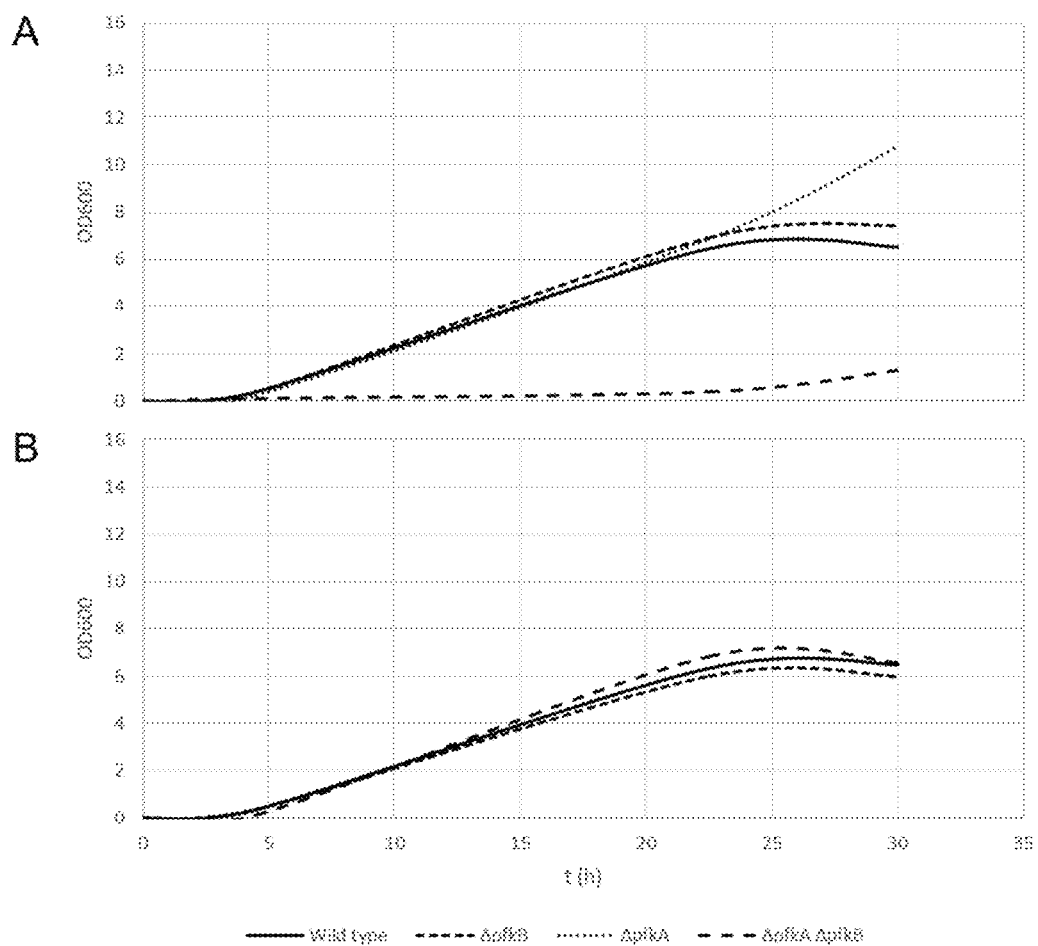
FIG. 4 displays growth characteristics of *E. coli* strains during cultivation on glucose (A) or a mixed-monosaccharide feedstock consisting of glucose and fructose (B) as sole carbon- and energy source.

FIG. 3 displays schematically another exemplary microbial cell of the invention capable of producing 2'-FL when cultivated on a mixed feedstock consisting of glucose (Glu) and fructose (Fru), but which mixed feedstock does not contain lactose (Lac). In addition to the exemplary microbial cell shown in FIG. 2, the microbial cell further comprises a fructose-specific Pts system (PtsF). Said PtsF system imports and phosphorlylates Fru to provide Fru-1-P. Fru-1-P is phosphorlyted by FruK to provide Fru-1,6-bisP. The microbial cell possesses fructose-1,6-bisphosphatase (GlpX) activity. Thereby, the genetically engineered microbial cell is metabolically engineered such that fructose and/or fructose-1-P can be utilized by the cell for UDP-Gal biosynthesis.

In addition, the phosphofructokinase gene(s) are deleted or functionally inactivated such that the cell does not possess phosphofructokinase (PfkA/PfkB) activity. Deletion or functional inactivation of the phosphofructokinase genes impairs conversion of Fru-6P to Fru-1,6-P such that utilization of Fru-6-P for generating energy-rich triphosphates is prevented and production of 2'-FL is enhanced.

EXAMPLES

Example 1—Preparation of a Mixed Monosaccharide Feedstock

A 50% (w/v) sucrose solution was prepared by dissolving 500 g of sucrose in water. The final volume of the solution was 1 litre. At a temperature of 30° C. to 35° C. the pH was adjusted by using 96% (v/v) sulfuric acid. Afterwards, the solution was sterilized in a vertical autoclave (Systec VX-65, Linden, Germany) at 121° C. for 45 minutes. Samples were taken before and after heat sterilization and kept frozen prior to analysis by high performance liquid chromatography (HPLC). HPLC was carried out using a RID-10A refractive index detector (Shimadzu, Germany) and a Waters XBridge Amide Column 3.5 μm (250×4.6 mm) (Eschborn, Germany) connected to a Shimadzu HPLC system. Isocratic elution was carried out with 30% solvent A (50% (v/v) acetonitrile in double distilled water, 0.1% (v/v) NH4OH) and 70% solvent B (80% (v/v) acetonitrile in double distilled water, 0.1% (v/v) NH4OH) at 35° C. and at a flow rate of 1.4 mL min-1. Samples were cleared by solid phase extraction on an ion exchange matrix (Strata ABW, Phenomenex). Ten microliters of the sample (dilution of 1:5) was applied to the column. Finally, the relative amount of detected sugars was determined. As depicted in Table 1, the sucrose conversion into the monosaccharides glucose and fructose increased with decreasing pH values of the solutions prior to heat treatment. Full sucrose cleavage could be observed at pH values≤3.50 when acidification was carried out with sulfuric acid.

TABLE 1

Relative amount of sugars detected in pH adjusted 50% (w/v) sucrose solution before and after heat sterilization. The pH adjustment was carried out using 96% (v/v) sulfuric acid. Depicted is the percental amount of sugars (area under the curve; AUC) detected by HPLC.

| | Relative composition [%] | | |
|---|---|---|---|
| pH | Sucrose | Glucose | Fructose |
| before heat sterilization | | | |
| 3.50-7.10 | 100 | — | — |
| after heat sterilization | | | |
| 7.10 (not acidified) | 100 | — | — |
| pH 5.50 | 87.55 | 6.30 | 6.15 |
| pH 5.05 | 68.25 | 16.62 | 15.13 |
| pH 3.87 | 13.90 | 45.05 | 41.06 |
| pH 3.50 | — | 51.68 | 48.32 |

Example 2—Feedstock-Dependent Growth of Various Gene Deletion Strains

The growth behavior of an E. coli BL21(DE3) strain (wild type) as well as the mutated strains E. coli pfkA⁻ (ΔpfkA), E. coli pfkB⁻ (ΔpfkB), E. coli pfkA⁻ pfkB⁻ (ΔpfkA ΔpfkA) was compared. Genomic deletions were performed according to the method of Datsenko and Wanner (Proc. Natl. Acad. Sci. USA 97:6640-6645 (2000)). All strains were cultivated at 30° C. in 100 mL-shake flasks with 20 mL mineral salts medium, containing 7 g·L$^{-1}$ NH$_4$H$_2$PO$_4$, 7 g·L$^{-1}$ K$_2$HPO$_4$, 2 g·L$^{-1}$ KOH, 0.3 g·L$^{-1}$ citric acid, 2 g·L$^{-1}$ MgSO$_4$×7·H$_2$O and 0.015 g·L$^{-1}$ CaCl$_2$×6-H$_2$O, supplemented with 1 mL·L$^{-1}$ trace element solution (54.4 g·L$^{-1}$ ammonium ferric citrate, 9.8 g·L$^{-1}$ MnCl$_2$×4·H$_2$O, 1.6 g·L$^{-1}$ COCl$_2$×6·H$_2$O, 1 g·L$^{-1}$ CuCl$_2$×2·H$_2$O, 1.9 g·L$^{-1}$ H$_3$BO$_3$, 9 g·L$^{-1}$ ZnSO$_4$×7·H$_2$O, 1.1 g·L$^{-1}$ Na$_2$MoO$_4$×2·H$_2$O, 1.5 g·L$^{-1}$ Na$_2$SeO$_3$, 1.5 g·L$^{-1}$ NiSO$_4$×6·H$_2$O) and containing either 2% (m/v) glucose (A) or 1% (w/v) glucose/1% (w/v) fructose (B) as carbon source. Cultures were inoculated to OD 0.1 and growth development was monitored over 26 hours by OD$_{600}$ measurement. As shown in FIG. 2, E. coli pfkA⁻ pfkB⁻ hardly showed growth when glucose was provided as sole carbon- and energy source, whereas its growth was indistinguishable from the wild type strain as well as the single deletion mutants when the mixed monosaccharide feedstock was available.

Example 3—Total Fermentation of 2'-Fucosyllactose by an Engineered E. coli Strain During Growth on a Mixed-Monosaccharide Feedstock An E. coli BL21 (DE3) strain exhibiting the genotype pfkA⁻, lacZ⁻, fuclK⁺, wcaJ⁻, glk⁻, gcd⁻, ptsG⁻ was further genetically engineered by overexpressing enzymes for the de novo synthesis of GDP-Fucose (ManB, ManC, Gmd, WcaG), the 2'-fucosyltransferase gene wbgL from E. coli: O126, the sugar efflux transporter gene yberc0001_9420 from Yersinia bercovieri ATCC 43970, the glucose facilitator gene glf from Zymomonas mobilis, the β-1,4-galactosyltransferase gene galTpm1141 from Pasteurella multocida (GenBank: AEC04686) as well as the E. coli genes galE and pgm, encoding a UDP-glucose 4-epimerase and a phosphoglucomutase, respectively. Genomic deletions were performed according to the method of Datsenko and Wanner (Proc. Natl. Acad. Sci. USA 97:6640-6645 (2000)).

Genomic integration of heterologous genes was performed by transposition. Either the EZ-Tn5TM transposase (Epicentre, USA) was used to integrate linear DNA-fragments or the hyperactive C9-mutant of the mariner transposase Himar1 (Proc. Natl. Acad. Sci. 1999, USA 96:11428-11433) was employed for transposition. The genes were codon-optimized for expression in E. coli and prepared synthetically by GenScript cooperation.

The resulting E. coli strain was cultivated at 30° C. in a 3 L fermenter (New Brunswick, Edison, USA) starting with 1000 mL mineral salts medium containing 7 g·L$^{-1}$ NH$_4$H$_2$PO$_4$, 7 g·L$^{-1}$ K$_2$HPO$_4$, 2 g·L$^{-1}$ KOH, 0.3 g·L$^{-1}$ citric acid, 2 g·L$^{-1}$ MgSO$_4$×7·H$_2$O and 0.015 g·L$^{-1}$ CaCl$_2$×6·H$_2$O, supplemented with 1 mL·L$^{-1}$ trace element solution (54.4 g·L$^{-1}$ ammonium ferric citrate, 9.8 g·L$^{-1}$ MnCl$_2$×4·H$_2$O, 1.6 g·L$^{-1}$ COCl$_2$×6·H$_2$O, 1 g·L$^{-1}$ CuCl$_2$×2·H$_2$O, 1.9 g·L$^{-1}$ H$_3$BO$_3$, 9 g·L$^{-1}$ ZnSO$_4$×7·H$_2$O, 1.1 g·L$^{-1}$ Na$_2$MoO$_4$×2·H$_2$O, 1.5 g·L$^{-1}$ Na$_2$SeO$_3$, 1.5 g·L$^{-1}$ NiSO$_4$×6·H$_2$O) and containing 2% (m/v) hydrolyzed sucrose as carbon source. Cultivation was started with the addition of a 2.5% (v/v) inoculum from a pre-culture grown in the same medium. The end of the batch phase was characterized by a rise in the dissolved oxygen level. A carbon feed consisting of fully hydrolyzed sucrose, supplemented with 2 g·L$^{-1}$ MgSO$_4$×7·H$_2$O, 0.015 g·L$^{-1}$ CaCl$_2$×6·H$_2$O and 1 mL·L$^{-1}$ trace element solution, was applied instantaneously after leaving the batch phase. A feeding rate of 12.0-15.0 mL·L$^{-1}$·h$^{-1}$ was applied, referring to the starting volume. Aeration was maintained at 3 L·min$^{-1}$. Dissolved oxygen was maintained at 20-30% saturation by controlling the rate of agitation. The pH was maintained at 6.7 by adding 25% ammonia solution. Cultivation lasted for 86 hours and yielded substantial amounts of 2'-FL in the culture supernatant.

The invention claimed is:

1. A method for production of lactose or an oligosaccharide of interest which comprises a galactose-β1,4-glucose moiety at its reducing end, the method comprising:
   a) providing a genetically engineered microbial cell, wherein said microbial cell comprises:
      at least one glucose transporter for translocating glucose from the culture medium into the microbial cell's cytoplasm;
      an UDP-galactose biosynthesis pathway;
      at least one β-1,4-galactosyltransferase being able to galactosylate free glucose to intracellularly produce lactose; and
      one or more of:
      i) a fructose transporter, fructokinase-6 activity, and 6-phosphofructokinase-1 activity; and
      ii) a fructose specific phosphotransferase system and 1-phosphofructokinase;
   b) cultivating the microbial cell in a culture medium and under conditions that are permissive for production of said lactose or oligosaccharide of interest, wherein the culture medium comprises a mixture of glucose and fructose as main carbon source; and
   c) recovering the lactose or oligosaccharide of interest from the culture medium and/or the microbial cell.

2. The method according to claim 1, wherein the oligosaccharide of interest is a human milk oligosaccharide selected from 2'-fucosyllactose, 3-fucosyllactose, 2',3-difucosyllactose, 3'-sialyllactose, 6'-sialyllactose, 3-fucosyl-3'-sialyllactose, lacto-N-tetraose, lacto-N-neotetraose, lacto-N-fucopentaose I, lacto-N-fucopentaose II, lacto-N-fucopentaose III, lacto-N-fucopentaose V, lacto-N-difucosylhexose I, lacto-N-difucosylhexaose II, lacto-N-sialylpentaose LSTa, LSTb, LSTc.

3. The method according to claim 1, wherein the microbial cell is cultivated without exogenous supply of lactose.

4. The method of claim 1, wherein the mixture of glucose and fructose is obtained by hydrolyzation of sucrose.

5. The method of claim 1, wherein the at least one glucose transporter is selected from glucose facilitated diffusion proteins and glucose translocating permeases.

6. The method of claim 1, wherein said microbial cell expresses or overexpresses at least one gene encoding the glucose transporter.

7. The method of claim 6, wherein the microbial cell expresses or overexpresses at least one gene selected from glf, galP and functional variants thereof.

8. The method of claim 1, wherein said microbial cell possesses a phosphoglucomutase, a UTP-glucose-1-phosphate-uridyltransferase, and a UDP-glucose 4-epimerase.

9. The method of claim 1, wherein the β-1,4-galactosyltransferase is encoded by a gene selected from Neisseria meningitidis lgtB, Aggregatibacter aphrophilus lex-1, Pasteurella multocida galTpm1141 and functional variants thereof.

10. The method of claim 1, wherein said microbial cell possesses at least one additional glycosyltransferase.

11. The method of claim 10, wherein the at least one additional glycosyltransferase is selected from fucosyltransferases, sialyltransferases, glucosaminyltransferases and galactosyltransferases.

12. The method of claim 11, wherein the additional glycosyltransferase is a fucosyltransferase, and wherein said microbial cell possesses a mannose-6-phosphate isomerase, a phosphomannomutase, a mannose-1-phosphate-guanylyltransferase, a GDP-mannose-4,6-dehydratase, a GDP-L-fucose synthase.

13. The method of claim 1, wherein the microbial cell comprises a glucose-translocating phosphotransferase system.

14. The method of claim 1, wherein the microbial cell comprises a fructose-1,6-bisphosphatase.

15. The method of claim 1, wherein said microbial cell comprises a deletion or functional inactivation of a glucose-6-phosphate isomerase.

16. The method of claim 1, wherein said microbial cell comprises an exporter protein or a permease exporting the oligosaccharide of interest from the cell.

17. The method of claim 16, wherein said microbial cell comprises a sugar efflux transporter.

18. The method of claim 1, wherein said microbial cell is a bacterial cell selected from bacteria of the genera Escherichia, Lactobacillus, Corynebacterium, Bacillus, Streptococcus, Enterococcus, Lactococcus and Clostidium.

19. The method of claim 18, wherein the microbial cell is a bacterial cell selected from bacterial species of Escherichia coli, Corynebacterium glutamicum, Clotridium cellulolyticum, Clostridium ljungdahlii, Clostridium autoethanogenum, Clostridium acetobutylicum, Bacillus subtilis, Bacillus megaterium, Lactobacillus casei, Lactobacillus acidophilus, Lactobacillus helveticus, Lactobacillus delbrueckii, and Lactococcus lactis.

* * * * *